United States Patent
Fadler (10) Patent No.: US 7,899,155 B2
(45) Date of Patent: Mar. 1, 2011

(54) STAND FOR HOLDING A RADIATION DETECTOR FOR A RADIATION THERAPY DEVICE

(75) Inventor: Franz Fadler, Hetzles (DE)

(73) Assignee: Siemens Aktiengessellschaft, Munich (DE)

( * ) Notice: Subject to any disclaimer, the term of this patent is extended or adjusted under 35 U.S.C. 154(b) by 266 days.

(21) Appl. No.: 12/089,686

(22) PCT Filed: Oct. 4, 2006

(86) PCT No.: PCT/EP2006/067043
§ 371 (c)(1),
(2), (4) Date: Apr. 24, 2008

(87) PCT Pub. No.: WO2007/042440
PCT Pub. Date: Apr. 19, 2007

(65) Prior Publication Data
US 2008/0279339 A1 Nov. 13, 2008

(30) Foreign Application Priority Data
Oct. 14, 2005 (DE) .......................... 10 2005 049 684

(51) Int. Cl.
*A61N 5/10* (2006.01)
(52) U.S. Cl. ........................................ 378/65; 378/189
(58) Field of Classification Search ..................... 378/65, 378/167, 189
See application file for complete search history.

(56) References Cited

U.S. PATENT DOCUMENTS

| 4,879,737 A | * | 11/1989 | Grady ........................... 378/196 |
| 5,142,559 A | | 8/1992 | Wielopolski et al. |
| 6,304,627 B1 | * | 10/2001 | Horbaschek ..................... 378/19 |
| 6,341,156 B1 | | 1/2002 | Baetz et al. |
| 6,865,254 B2 | | 3/2005 | Näfstadius |

(Continued)

FOREIGN PATENT DOCUMENTS
EP 0 547 377 6/1993
(Continued)

OTHER PUBLICATIONS
Translation for EP 547377 A2 published on Jun. 23, 1993.*
(Continued)

*Primary Examiner* — Chih-Cheng G Kao
(74) *Attorney, Agent, or Firm* — Brinks Hofer Gilson & Lione (57) ABSTRACT

Stand for holding a radiation detector for a radiation therapy device, as well as a radiation therapy device having a stand for holding a radiation detector. In order to integrate a radiation detector in a space-saving manner in a radiation therapy device, a stand is provided in order to hold the radiation detector, such that the radiation detector can be moved in a linear-movement direction and can be pivoted about a pivoting axis; the radiation therapy device has a gantry, a first radiation source and the stand, using which the radiation detector can be moved to at least one examination position within the radiation area of the first radiation source and can be moved to a parked position, outside the radiation area, in the opposite direction to a first radiation direction from the first radiation source, with respect to the examination position.

30 Claims, 8 Drawing Sheets

U.S. PATENT DOCUMENTS

| | | | |
|---|---|---|---|
| 6,888,919 B2 | 5/2005 | Graf | |
| 7,147,373 B2 | 12/2006 | Cho et al. | |
| 2003/0091150 A1* | 5/2003 | Barber et al. | 378/189 |
| 2003/0147504 A1* | 8/2003 | Hanover | 378/197 |
| 2004/0005027 A1* | 1/2004 | Nafstadius | 378/65 |
| 2004/0068169 A1 | 4/2004 | Mansfield et al. | |
| 2004/0258195 A1* | 12/2004 | Hara | 378/11 |

FOREIGN PATENT DOCUMENTS

| | | |
|---|---|---|
| EP | 1 479 411 | 11/2004 |
| WO | WO 2004/004829 A1 | 1/2004 |
| WO | WO 2004/033026 A2 | 4/2004 |
| WO | WO 2004/033026 A3 | 4/2004 |
| WO | WO 2005/015125 A1 | 2/2005 |

OTHER PUBLICATIONS

International Search Report, Jan. 31, 2007, for PCT/EP/2006/067043.

PCT Written Opinion, Jan. 31, 2007 (with English Translation).

German Office Action for DE 10 2005 049 684.9-52 dated Sep. 13, 2007 and English translation.

PCT Written Report and English translation for PCT/EP2006/067043 dated Jan. 31, 2007.

Max Pollermann, "Bauelemente der Physikalischen Technik", Springer-Verlag Berlin Heidelberg, New York 1972, pp. 94-108.

* cited by examiner

STAND FOR HOLDING A RADIATION DETECTOR FOR A RADIATION THERAPY DEVICE

The present patent document is a nationalization of PCT Application Serial Number PCT/EP2006/067043, filed Oct. 4, 2006, designating the United States, which is hereby incorporated by reference. This application also claims the benefit of DE 10 2005 049 684.9, filed Oct. 14, 2005 which is hereby incorporated by reference.

BACKGROUND

The present embodiments relate to a stand for holding a radiation detector for a radiation therapy device.

Radiation therapy devices are used in medicine to treat diseased tissue, such as tumor tissue, with ionizing radiation. During radiation therapy, radiation is used. The radiation may be, for example, high-energy X-ray radiation, radiation composed of lightweight particles, such as electrons or positrons, or radiation composed of heavy particles, such as protons or ions. During radiation therapy, it is desired that only the diseased tissue is specifically bombarded, while the surrounding, healthy tissue is mostly not irradiated.

The respective treatment area is positioned as exactly as possible relative to the radiation therapy device in order to only irradiate the diseased tissue. The radiation is aligned and delineated as exactly as possible with respect to the irradiation area. A radiation detector, which uses the therapeutic radiation to produce an image of the irradiation area or its surrounding area, may be used for positioning of the treatment area and for alignment and delineation of the therapeutic radiation. Because of its high quantum energy, the therapeutic radiation is scattered to a greater extent about the treatment area and the tissue surrounding this treatment area than diagnostic radiation, whose quantum energy is lower, so that this type of imaging has comparatively low contrast. Diagnostic X-ray radiation may have a maximum quantum energy of 150 kiloelectron volts (KeV) while, in contrast, therapeutic X-ray radiation typically has a quantum energy in the region of a megaelectron volt (MeV).

U.S. Pat. No. 6,888,919 B2 discloses an additional, diagnostic X-ray imaging system that is used for exact positioning of the tumor. The X-ray imaging system includes an X-ray source for production of low-energy diagnostic X-ray radiation and a radiation detector for diagnostic imaging based on detection of the diagnostic X-ray radiation. U.S. Pat. No. 6,888,919 B2 also discloses a radiation therapy device in which the therapeutic radiation source is arranged on a gantry that can be rotated around a horizontal axis in order to allow the therapeutic radiation to be aligned flexibly relative to the patient.

In order to allow the diseased tissue to be positioned as freely as possible, the gantry and the components arranged on this gantry are compact. The distance from the radiation head to the isocenter of the radiation therapy device should be as great as possible. The radiation head may include the therapeutic radiation source and at least one collimator for beamforming. Particularly in the case of radiation therapy devices with an additional diagnostic X-ray imaging system, the lack of space represents a major problem for the design configuration of the radiation therapy device.

U.S. Pat. No. 6,888,919 B2 discloses a radiation therapy device. The radiation therapy device includes a first and second gantry. The first gantry can be rotated about an axis and has a therapeutic radiation source. The second gantry can be rotated about the same axis and has a diagnostic radiation source on one side and a radiation detector for imaging on the other side. The radiation detector is a multi-energy imaging unit that can produce an image both on the basis of the therapeutic radiation and on the basis of the diagnostic radiation. The diagnostic X-ray emitter may be moved in and out. To produce an image based on the diagnostic X-ray radiation, the first gantry is pivoted with the therapeutic radiation source to the side with respect to the second gantry with the diagnostic radiation source, so that the diagnostic radiation source can be moved out. To treat the diseased tissue with the therapeutic radiation, the diagnostic X-ray radiation source is moved in, and the therapeutic X-ray radiation source together with the gantry is pivoted to the previous position of the moved-out, diagnostic X-ray radiation source. A diagnostic image of the diseased tissue is produced first with the moved-out diagnostic X-ray radiation source, from a viewing angle that corresponds to the radiation direction of the subsequent radiation treatment using the therapeutic radiation source. The free space for positioning and alignment of the patient to be treated is restricted because of the additional second gantry. The radiation therapy device design is complicated.

SUMMARY AND DESCRIPTION

The present embodiments may obviate one or more of the drawbacks or limitations inherent in the related art. For example, one embodiment integrates a radiation detector in a space-saving manner in a radiation therapy device.

In one embodiment, a stand for holding a radiation detector for a radiation therapy device is provided. The stand includes a mount, an intermediate part that is arranged on the mount, such that it can be moved in a lifting direction relative to the mount, and an arm that is arranged on the intermediate part, such that it can pivot relative to the intermediate part about a pivoting axis essentially parallel to the lifting direction, and has a holding apparatus for holding a flat radiation detector essentially at right angles to the lifting direction.

The stand may move in a lifting direction as a first mechanical degree of freedom and pivot about a pivoting axis essentially parallel to the lifting direction as a second mechanical degree of freedom allows the radiation detector to be positioned in a space-saving manner. The design configuration in just three parts and with only two mechanical degrees of freedom allows the stand to be compact and allows the radiation detector to be positioned flexibly. The stand provides a high degree of mechanical stability and exact positioning capability because of the small amount of mechanical play in the degrees of freedom.

The stand may include at least one lifting rail. The mount and/or the intermediate part may include at least one lifting rail for guidance of the intermediate part. The intermediate part may be moved relative to the mount part using the at least one lifting rail. The stand is highly robust with particularly exact movement guidance, free of mechanical play, during movement of the intermediate part in the lifting direction.

The stand may include a lifting drive rod, which is powered by external power, in order to move of the intermediate part allows a simple drive for this movement along the lifting direction. A motor may be arranged on the mount and/or the intermediate part in order to move the intermediate part relative to the mount by external power.

In one embodiment, the drive rod and/or the lifting rail may be arranged both on the mount and on the intermediate part.

The intermediate part and/or the arm may be designed such that the arm can be pivoted by external power relative to the intermediate part. The pivoting movement may be controlled.

A motor may be arranged either on the intermediate part or on the arm for pivoting by external power.

The arm may include a holding apparatus for holding the radiation detector. The holding apparatus may be arranged such that the holding apparatus can be moved relative to the arm in a movement direction essentially at right angles to the lifting direction of the intermediate part of the stand. The respective viewing angle may be varied during production of an image with the radiation detector. The production of a three-dimensional image of the tissue to be treated may be based on the production of a plurality of images from different viewing angles.

The arm may include at least one holding rail for guidance of the holding apparatus. The radiation detector may be held in a robust manner with little mechanical play while the radiation detector is being moved along the movement direction. The holding apparatus may form an interlocking arrangement on at least one holding rail of the radiation detector.

In one embodiment, the arm may include a drive belt powered by external power or a drive chain powered by external power for movement of the holding apparatus. The holding apparatus for the radiation detector may be moved along the movement direction. The drive belt or the drive chain may be driven by a motor, which can be arranged on the holding part.

The arm may include a movement drive rod that is powered by external power for movement of the holding apparatus and/or for movement of the radiation detector. The movement drive rod provides a simple drive for linear movement along the movement direction. A motor is arranged on the arm for externally powered movement of the holding apparatus and of the radiation detector relative to the arm. It is feasible for the movement drive rod to have a gearwheel, which engages in an interlocking manner in a toothed rail on the holding apparatus or on the radiation detector.

The mount for arrangement on a gantry of a radiation therapy device with a first radiation source for production of first radiation that may be emitted in a first radiation direction makes it possible to use the stand in a radiation therapy device. For example, an existing radiation therapy device may be retrofit with a stand for holding the radiation detector. The lifting direction may be essentially parallel to the first radiation direction. By way of example, the first radiation source may be a therapeutic radiation source for the production of X-ray radiation in the MeV energy range, of electron radiation, or proton radiation.

In one embodiment, the radiation detector, which can be held on the holding apparatus, may be pivoted and/or moved to at least one examination position within the radiation area of the first radiation source. A diagnostic record of the body tissue located within a target volume of the radiation therapy device may be produced from a viewing angle that corresponds essentially to the perspective of the first radiation source. This allows the diseased body tissue, which is to be treated, to be positioned particularly accurately in the target volume.

In one embodiment, the radiation detector may be located in front of the first radiation source in the first radiation direction and may be located together with the first radiation source on the same side relative to the target volume. This position may be the examination position. A second radiation source may be arranged on the opposite side relative to the target volume, emitting second radiation through the target volume in the direction of the radiation detector. The first radiation source may produce high-energy therapeutic radiation, while the second radiation source produces low-energy diagnostic radiation.

In one embodiment, the radiation detector may be moved to different examination positions within the radiation area of the first radiation source, for example, at different distances from the first radiation source. Different beamforming elements may be replaced or combined with other beamforming elements. Beamforming elements may be arranged between the first radiation source on the one side and the radiation detector on the other side.

In one embodiment, the radiation detector, which may be arranged on the holding apparatus, may be pivoted out of the radiation area of the first radiation source. The radiation detector may be removed from the radiation area, for example, to carry out a radiation-therapy treatment using the first radiation source.

In one embodiment, the radiation detector may be moved outside the radiation area of the first radiation source. The radiation detector may be moved to a parked position, which is offset with respect to the examination position in the opposite direction to the first radiation direction. The parked position, which is different than the examination position, and in which the first radiation source is further away from the target volume, creates free space for positioning of the respective patient to be treated.

In one embodiment, the radiation detector, when in a parked position, may be positioned alongside the first radiation source essentially at right angles to the first radiation direction in a lateral direction.

A radiation therapy device may include a gantry on which the first radiation source and the stand for holding the radiation detector are arranged. An image of the respective target volume may be produced from the viewing angle of the first radiation source from an examination position of the radiation detector within the radiation area of the first radiation source, and the radiation detector may be positioned in a parked position, which is offset with respect to the examination position in the opposite direction to the first radiation direction, outside the radiation area.

The radiation detector may be narrower than a radiation source and be positioned in front of the first radiation source in the first radiation direction. Accordingly, there is no need to pivot the first radiation source away, which would be complex, in order to produce a diagnostic image of the target volume, as in U.S. Pat. No. 6,888,919 B2.

In one embodiment, the first radiation source produces the first radiation in the form of therapeutic radiation, for example, therapeutic X-ray radiation.

The first radiation source and the radiation detector may be arranged on the same side of the target volume, which can be irradiated with the first radiation, in the examination position.

A second radiation source, which is arranged on a side opposite the radiation detector relative to the target volume, makes it possible to use the radiation detector to produce an image of the tissue located in the target volume and of the tissue located in an area surrounding the target volume. The radiation source, which is arranged on the same side relative to the target volume, may produce therapeutic radiation.

In one embodiment, the stand for holding the radiation detector and the first radiation source for producing the therapeutic radiation may be located at one end of the gantry, and the second radiation source for producing diagnostic X-ray radiation may be located on the other side of the gantry. The stand may be aligned to detect second radiation emitted from the second radiation source in the direction of the radiation detector in the examination position when the radiation detector is in an examination position.

The holding apparatus may be moved relative to the stand in a movement direction essentially at right angles to the first radiation direction. This movement allows the viewing angle to be varied flexibly during production of the diagnostic image. A three-dimensional image of the target volume and of the tissue located in the area surrounding this target volume may be produced by producing a plurality of images from different viewing angles. The second radiation source may be pivoted about an axis at right angles to the first radiation direction and at right angles to the movement direction. In order to produce images from different viewing angles, the second radiation source is pivoted in synchronism with the linear movement of the holding apparatus for the radiation detector, such that the second radiation strikes the radiation detector throughout the entire irradiation time.

The second radiation source may produce the second radiation in the form of diagnostic radiation, for example, diagnostic X-ray radiation.

In one embodiment, the radiation detector detects the first radiation passing through the radiation detector. When in the examination position, the radiation detector may measure the radiation area and the intensity of the first radiation emitted from the first radiation source. Any attenuation of the first X-ray radiation, which may be produced by the patient who is to be treated, may be measured in combination with the second radiation detector on the side of the target volume opposite that of the abovementioned radiation detector. The attenuation makes it possible to deduce the total radiation energy absorbed in the patient when irradiated with the first radiation.

DETAILED DESCRIPTION

Figure 1:
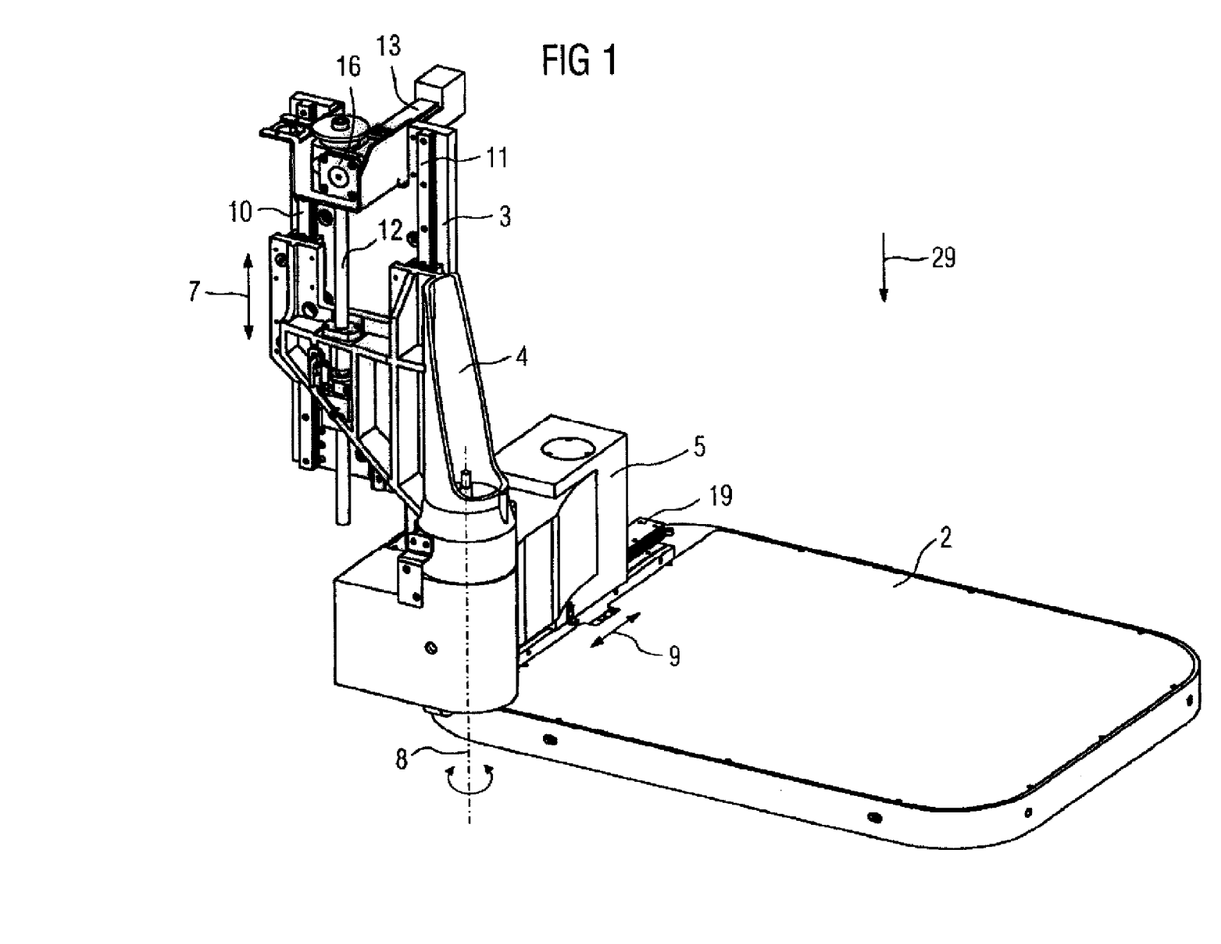
FIG. 1 illustrates one embodiment of a stand with a mount, an intermediate part, and an arm with a radiation detector in an examination position.

FIG. 1 shows a perspective illustration of a stand 1. The stand 1 may include a mount 3, an intermediate part 4 and an arm 5. Two holding apparatuses 6 for holding a flat radiation detector 2 may be arranged on the arm 5. The holding apparatuses 6 may be seen in FIGS. 2 and 3.

The mount 3 is arranged on a radiation therapy device, for example, on the gantry. The intermediate part 4 is arranged on the mount 3, such that the intermediate part 4 may be moved in a lifting direction 7, with two lifting rails 10 and 11 being arranged on the mount 3 for guidance of the intermediate part 4. A motor 13 is provided for external powered movement of the intermediate part 4 and convert a rotary movement via a direction-changing transmission 16 to a drive rod 12 with a thread. A mating thread and the intermediate part 4 engage in an interlocking manner.

The arm 5 is arranged on the intermediate part 4, such that it can pivot about a pivoting axis 8 that runs essentially parallel to the lifting direction 7. The drive mechanism for the pivoting movement of the arm 5 will be explained in more detail in the figure description relating to FIG. 3.

The holding apparatus 6 for the radiation detector 2 is arranged on the arm 5, such that the radiation detector 2 may move in a movement direction 9. The movement direction 9 runs essentially at right angles to the lifting direction 7. The method of operation of the holding apparatuses 6 and the drive mechanism for the movement will be explained in more detail in the figure description relating to FIGS. 3 and 4.

As shown in FIG. 1, the stand 1 is set such that the radiation detector 2 is arranged in its examination position. In the examination position, the radiation detector 2 is located with a first radiation source in its intended radiation area. The stand 1 is arranged with the radiation detector 2 on a radiation therapy device. The intended radiation direction 29 is aligned parallel to the lifting direction 7, and points downward in FIG. 1.

Figure 2:
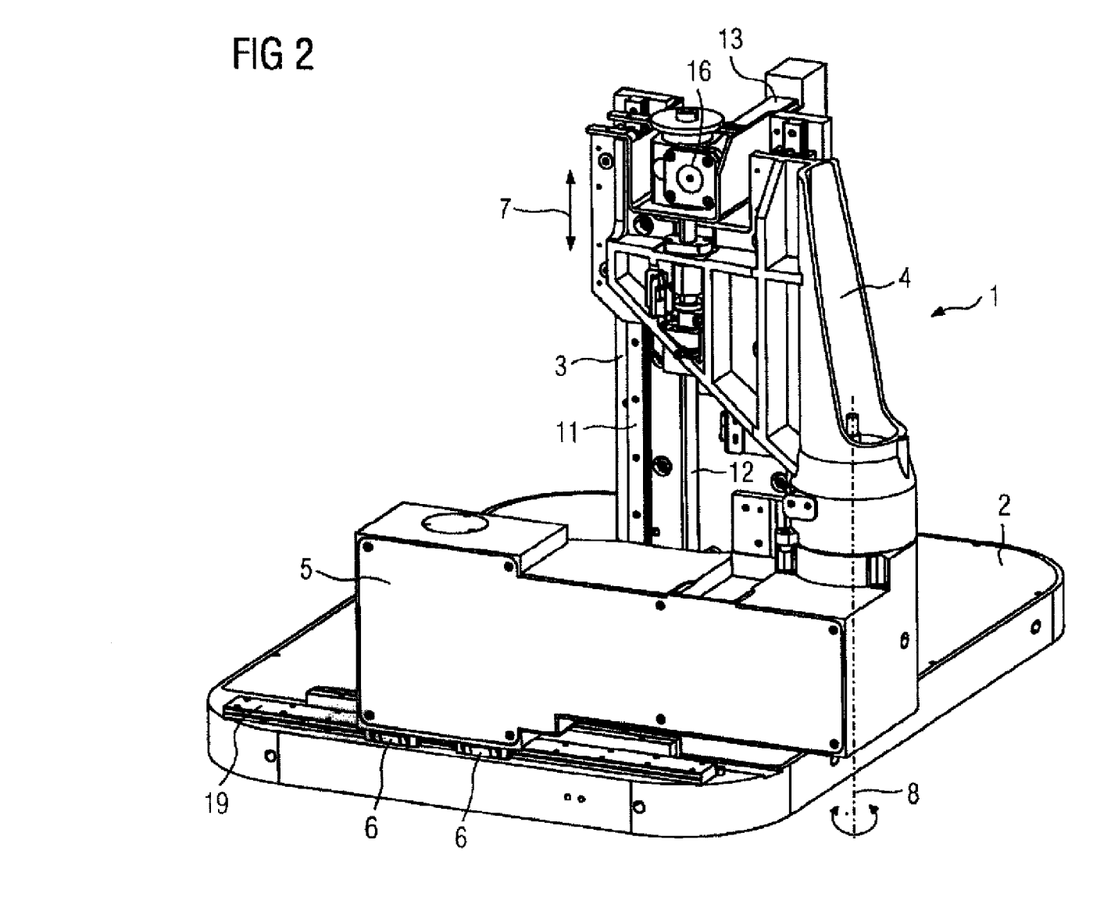
FIG. 2 illustrates the stand shown in FIG. 1, with the radiation detector being positioned in a parked position.

As shown in FIG. 2, the radiation detector 2 is positioned by a pivoting movement of the arm through 90° in the counterclockwise direction with respect to a plan view of the pivoting axis 8, and a lifting movement of the intermediate part 4 as far as the upper end of the mount part 3 to a parked position outside the intended radiation area.

Figure 3:
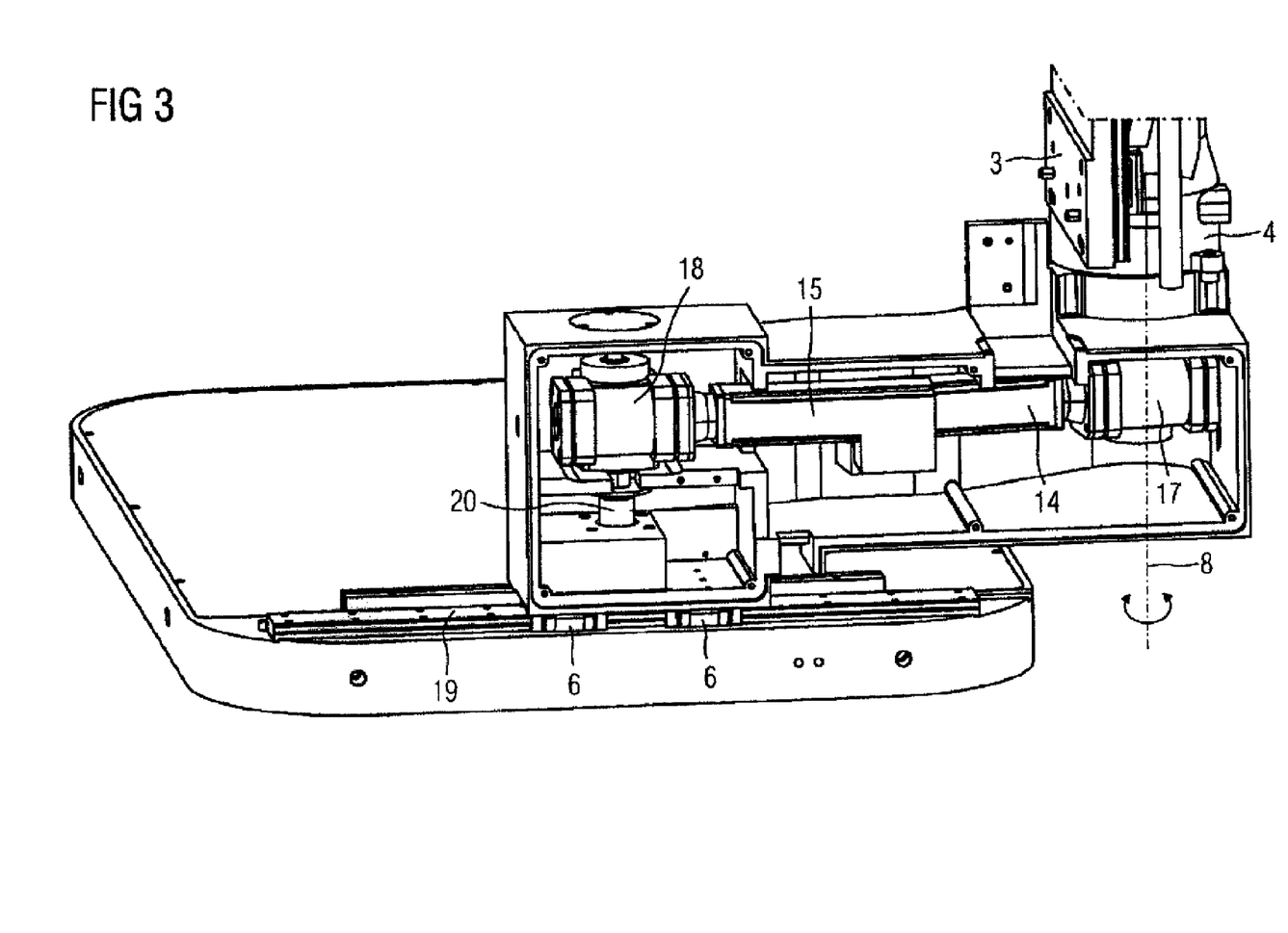
FIG. 3 illustrates the stand as shown in FIG. 1 from the rear.

FIG. 3 shows a detailed enlargement of a perspective illustration of the stand 1 from the rear. The stand 1 includes a housing cover. In FIG. 3, the housing cover at the rear of the arm part 5 is removed.

A drive motor 14 is arranged in/on the arm 5. The drive motor 14 provides a motor-powered pivoting movement of the arm part 5 relative to the intermediate part 4 by power being transmitted to the intermediate part 4 through a direction-changing transmission 17.

The arm 5 has a further motor 15 that drives the linear movement of the radiation detector 2 via a third direction-changing transmission 18 and via a movement drive rod 20.

Figure 4:
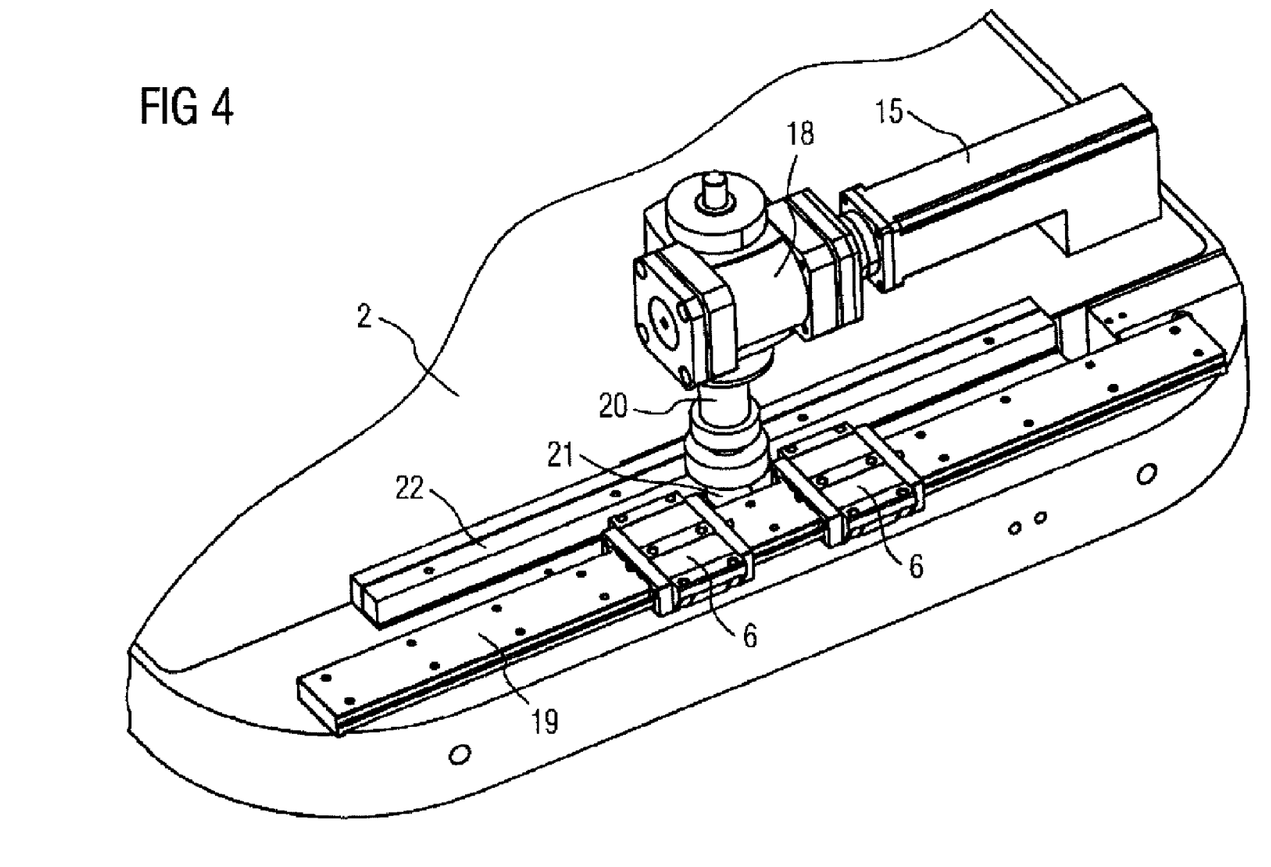
FIG. 4 illustrates the stand shown in FIG. 3 from the rear, with the housing of the arm part having been completely removed in order to illustrate the drive mechanism and a holding apparatus for the radiation detector.

As shown in FIG. 4, the arm 5 includes a further motor 15, the direction-changing transmission 18, the movement drive rod 20, and/or a gearwheel 21. The gearwheel 21 may be arranged coaxially on this movement drive rod 20 and engage in an interlocking manner in a toothed drive rail 22 of the radiation detector 2. The interlock between the gearwheel 21, which is driven indirectly by the motor 15, and the drive rail 22 converts a rotary movement of the motor 15, which is arranged in a fixed position relative to the housing of the arm 5, to a linear movement of the radiation detector 2.

As shown in FIG. 4, the holding apparatuses 6 which are attached to the outside of the housing of the arm 5. The holding apparatuses 6 surround the holding rail 19 in an interlocking manner.

Figure 5:
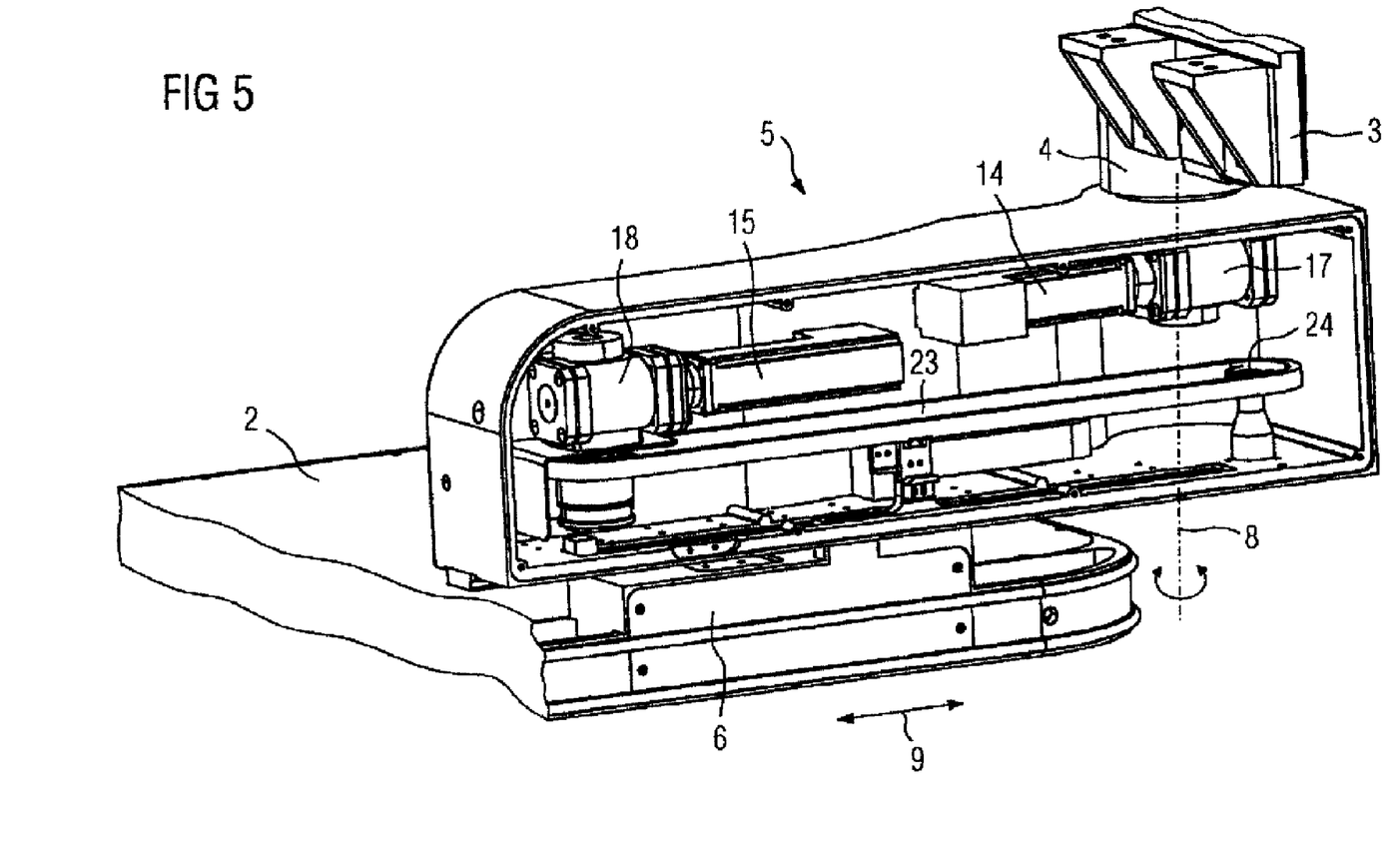
FIG. 5 illustrates another embodiment of the stand as shown in FIG. 3 from the rear, with a different drive mechanism and a different holding apparatus.

FIG. 5 shows a detailed enlargement of a perspective illustration of a further exemplary embodiment of the stand 1 shown in FIG. 1 from the rear. The stand 1 includes a drive mechanism, which has been modified in comparison to the previously described exemplary embodiment, for linear movement of the radiation detector. As in FIG. 3, the rear housing cover of the arm part 5 has been removed in order to show the drive mechanism.

The arm 5 includes a motor 15 that drives the linear movement of the radiation detector 2 via the third direction-changing transmission 18 and via a drive belt 23, which is passed over a guide roller 21 and is connected at one end to the holding apparatus 6 for the radiation detector 2.

Figure 6:
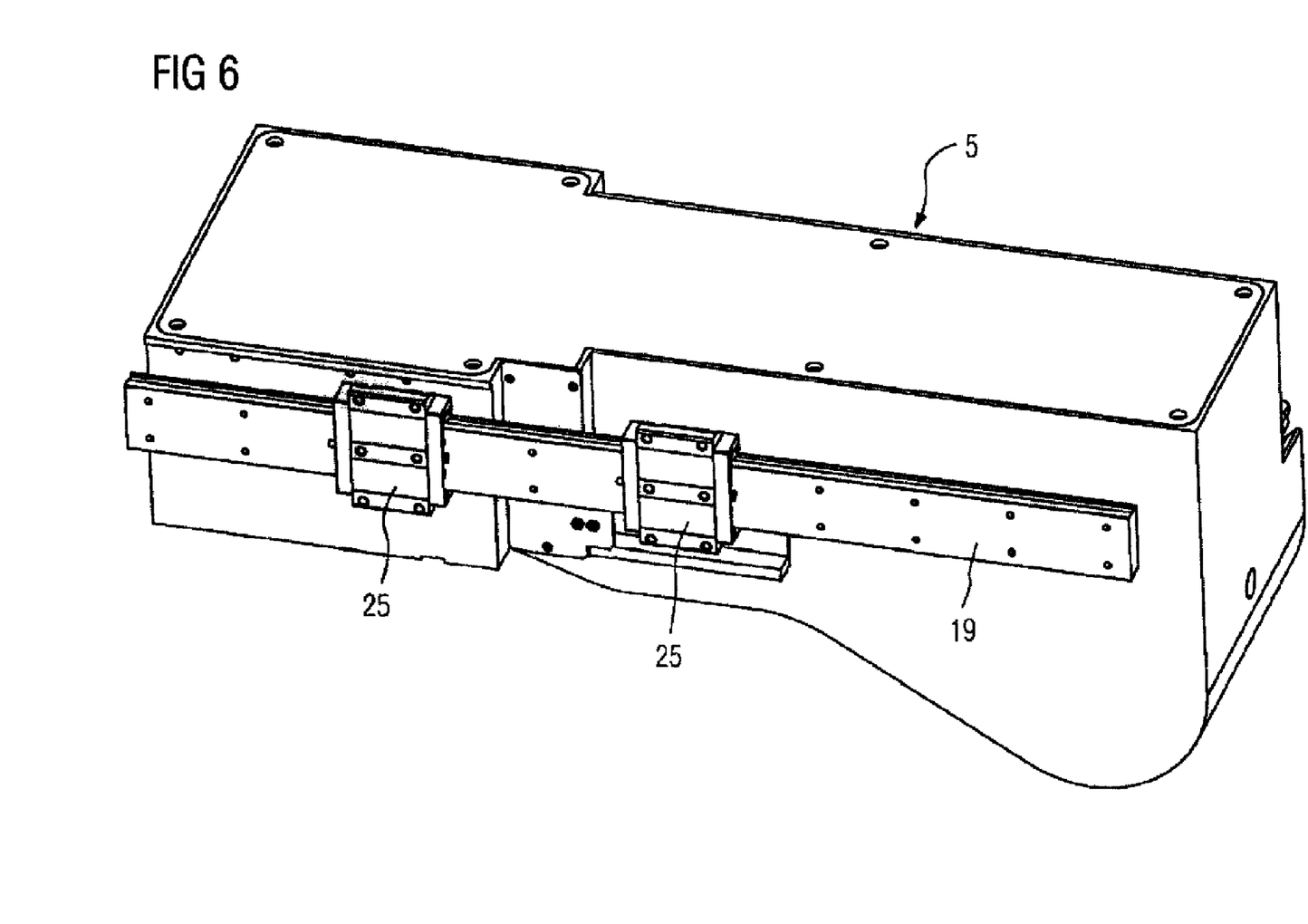
FIG. 6 illustrates another embodiment of the stand shown in FIG. 5, tilted forward, with a rail arranged on the arm.

FIG. 6 shows a perspective illustration of the arm 5 according to the exemplary embodiment illustrated in FIG. 5, tilted slightly forwards. The arm 5 includes a holding rail 19 for guidance of the holding apparatus 6 relative to the arm 5, with only two rail holders 25 of the holding apparatus 6 being illustrated. The two rail holders 25 surround the holding rail in an interlocking manner from two opposite sides. In order to allow the holding rail 19 and the rail holders 25 to be seen better, this figure does not show the majority of the holding apparatus or of the radiation detector.

Figure 7:
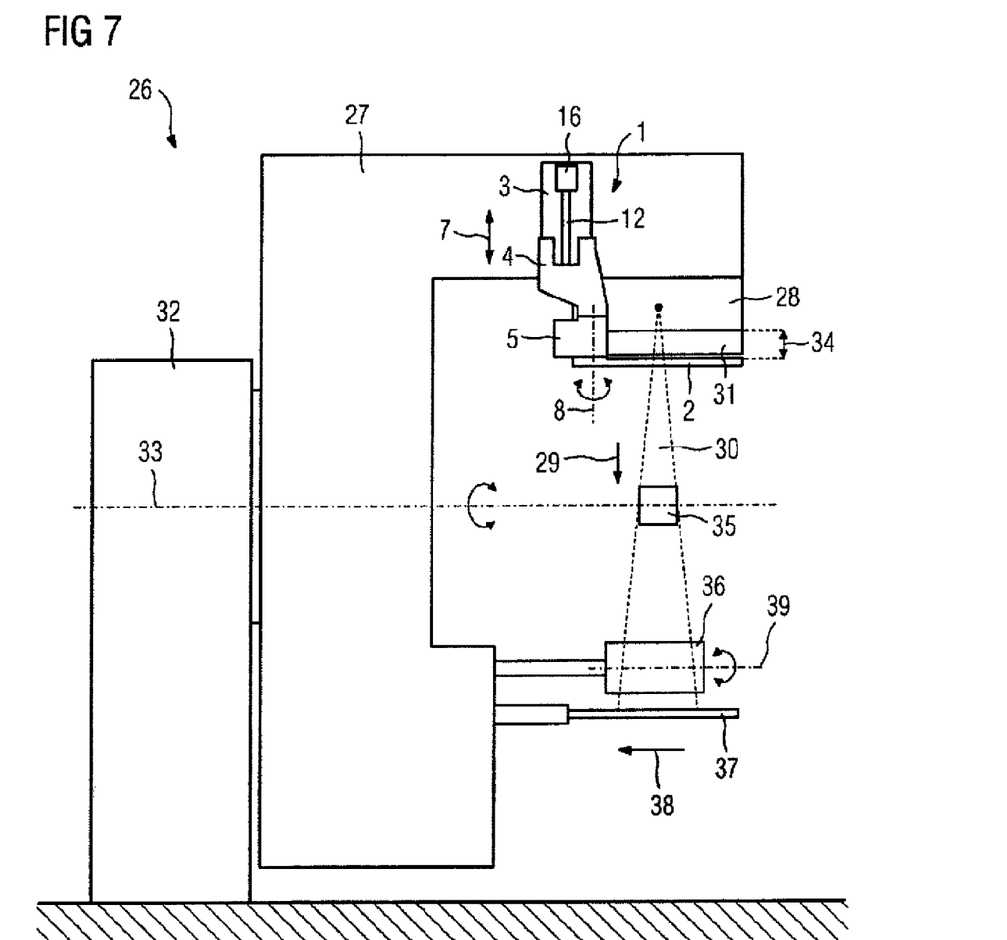
FIG. 7 illustrates one embodiment of a radiation therapy device with a gantry on which a first radiation source and the stand as shown in FIG. 1 together with the radiation detector are arranged, in the examination position under the first radiation source.

FIG. 7 shows a side view of a radiation therapy device 26 having a gantry 27, which is arranged on a base stand 32. The radiation therapy device 26 can rotate about a vertical rotation axis 33, having a first radiation source 28 arranged on the gantry 27 and having the stand 1, arranged on the gantry 27, with the radiation detector 2 for the examination shown in FIG. 1. The first radiation source 28 can emit the first radiation in the form of therapeutic X-ray radiation in the MeV energy range in the first radiation direction 29. The radiation detector is in the form of a matrix detector, which is located at least partially within the radiation area 30 of the first radiation source 28 in the illustrated examination position.

In one embodiment, in the examination position, the first radiation detector 28 is arranged at a distance 34 from the first radiation source 28, underneath it, in the first radiation direction 29. A beamforming apparatus is arranged between the first radiation source 28 on one side and the radiation detector 2 on the other side. The beamforming apparatus may be a "multileaf collimator" 31. The stand 1 is designed such that the radiation detector 2 is moved to different examination positions within the radiation area 30 of the first radiation source 28, each at different distances 34 from the first radiation source 28 in the lifting direction 7. Further beamforming apparatuses may be arranged in between the first radiation source 28 and the radiation detector 2. The "multileaf collimator" 31 may be replaced by some other beamforming device. The beamforming apparatuses may be omitted. In this exemplary embodiment, the lifting direction 7 is parallel to the first radiation direction 29.

In its examination position, both the first radiation source 28 and the radiation detector 2 are arranged on the same side relative to a target volume 35, which can be irradiated with the first radiation and is located in the region of the isocenter of the radiation therapy device 26. A second radiation source 36 is arranged on the opposite side relative to the target volume 35 and is intended to emit second radiation in the form of diagnostic X-ray radiation in the energy range predominantly below 125 keV, in the opposite direction to the first radiation to the radiation detector 2. The radiation detector 2 is designed such that, based on this second radiation, a diagnostic X-ray image of the target volume 35 and of an examination area which surrounds this target volume 35 can be produced. This X-ray image may be used to position and to align a patient to be treated relative to the target volume 35 and to constrain the radiation area 30 by a shutter.

The radiation detector 2 may be moved by the stand 1 in a movement direction 9, which runs at right angles to the plane of the illustration. In synchronism with this linear movement, the second radiation detector 36 may be tilted about a tilt axis 39 at right angles to the first radiation direction 29 and at right angles to the movement direction 9, so that the second radiation, which can be emitted from the second X-ray source 36, strikes the radiation detector 2 during its linear movement. The X-ray image, which is initially only two-dimensional, may be used to obtain information at right angles to the radiation direction 29 and over the examination area, relating to the three-dimensional tissue arrangement in the radiation direction 29. Two X-ray images with different imaging perspectives are used. After the at least one X-ray image has been recorded, the second radiation source 36 may be moved in a vertical direction 38 with respect to the gantry 27.

A further radiation detector 37 is arranged on the side opposite the radiation detector 2 relative to the target volume 35 and is designed to produce an X-ray image of the target volume 35 and/or of the examination area surrounding this target volume 35, based on the high-energy, first radiation. Any attenuation of the first radiation resulting from the patient, who is positioned, at least partially, in the target volume 35, may be determined by a development of the radiation detector 2, which is arranged underneath the first radiation source 28, in such a way that this is also suitable for detection of the high-energy first radiation, in combination with the further radiation detector 36 on the opposite side of the target volume 36. In addition to the second radiation source 36, the further radiation detector 38 may be moved in the vertical direction 38 with respect to the gantry 27.

Figure 8:
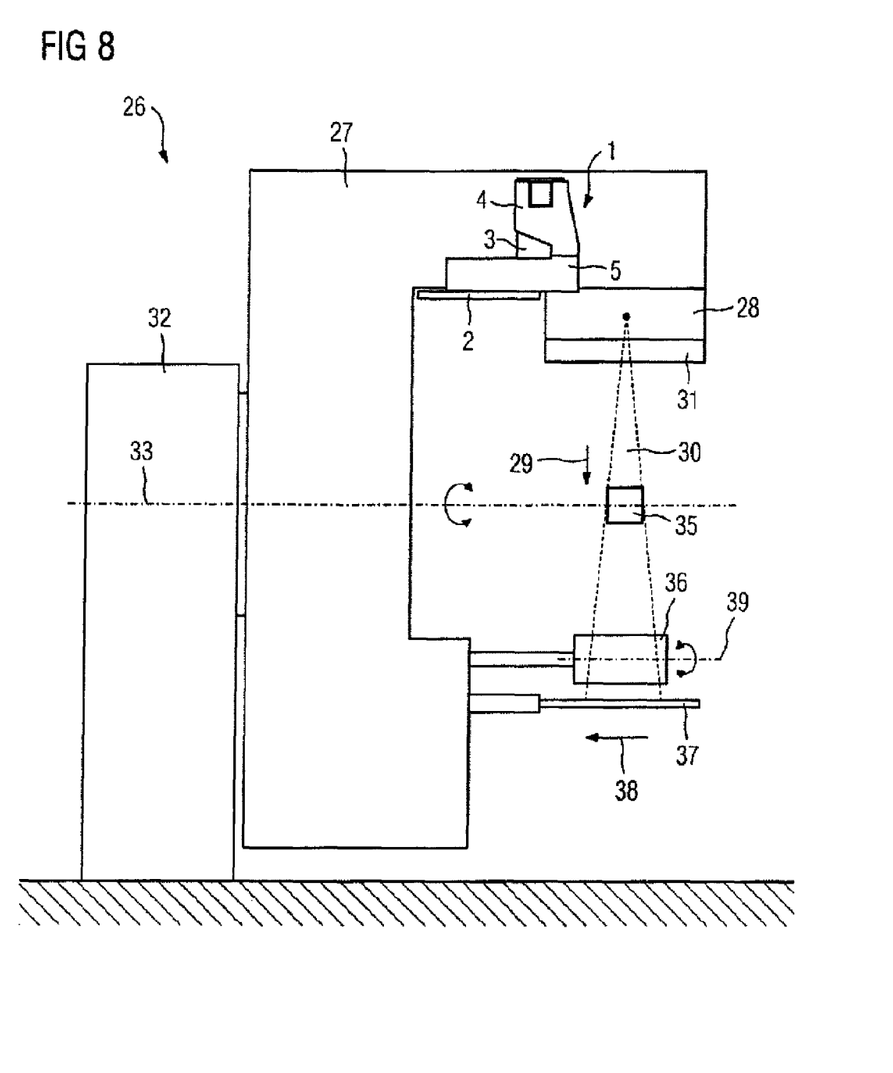
FIG. 8 illustrates another embodiment of the radiation therapy device as shown in FIG. 7, with the stand as shown in FIG. 2 with the radiation detector in the parked position alongside the first radiation source.

FIG. 8 shows a side view of the radiation therapy device 26 shown in FIG. 7, with the radiation detector 2 in its parked position shown in FIG. 2. The radiation detector 2 is offset with respect to the examination position in the opposite direction to the first radiation direction 29, outside the radiation area of the first radiation source. In the parked position, the radiation detector 2 is positioned alongside the first radiation source 28 in a lateral direction at right angles to the first radiation direction 29.

The gantry 27 may include cladding (covering) within which the radiation detector 2 is positioned, in its parked position, such that it cannot be seen from the outside.

In one embodiment, a radiation detector is integrated in a radiation therapy device. At least one stand holds the radiation detector, such that it may be moved in the lifting direction and may be pivoted about a pivoting axis. The radiation therapy device may include a gantry, a first radiation source and the stand. The radiation detector may be moved to at least one examination position within the radiation area of the first radiation source, and to a parked position, which is moved in the opposite direction to a first radiation direction from the first radiation source in comparison to the examination position, outside the radiation area.

The invention claimed is:

1. A stand for holding a radiation detector for a radiation therapy device, the stand comprising:
   a mount,
   an intermediate part arranged on the mount, the intermediate part being operable to be moved in a lifting direction relative to the mount,
   an arm arranged on the intermediate part, the arm being operable to pivot relative to the intermediate part about a pivoting axis essentially parallel to the lifting direction, and
   a holding apparatus arranged on the arm for holding a flat radiation detector essentially at right angles to the lifting direction,
   wherein the arm is operable to hold only the flat radiation detector, and
   wherein the holding apparatus is operable to be moved relative to the arm, such that the holding apparatus is moved in a movement direction essentially at right angles to the lifting direction.

2. The stand as claimed in claim 1, wherein the mount and/or the intermediate part includes at least one lifting rail for guidance of the intermediate part, which can be moved, relative to the mount.

3. The stand as claimed in claim 1, wherein the mount and/or the intermediate part includes a lifting drive rod that is powered by an external power to move the intermediate part.

4. The stand as claimed in claim 1, wherein the arm is operable to be pivoted by an external power.

5. The stand as claimed in claim 1, wherein the arm includes at least one holding rail for guidance of the holding apparatus.

6. The stand as claimed in claim 1, wherein the holding apparatus is interlocked on at least one holding rail of the radiation detector.

7. The stand as claimed in claim 1, wherein the arm includes a drive belt powered by external power, or a drive chain powered by external power, in order to move the holding apparatus.

8. The stand as claimed in claim 1, wherein the arm includes a movement drive rod powered by external power for movement of the holding apparatus and/or for movement of the radiation detector.

9. The stand as claimed in claim 1, wherein the mount is arranged on a gantry of a radiation therapy device including a first radiation source for production of first radiation that is operable to be emitted in a first radiation direction, which is essentially parallel to the lifting direction.

10. The stand as claimed in claim 9, wherein the radiation detector is operable to be held on the holding apparatus, the radiation detector being pivotable and/or movable to at least one examination position within the radiation area of the first radiation source.

11. The stand as claimed in claim 10, wherein the radiation detector is operable to be moved to different examination positions within the radiation area of the first radiation source, the different examination positions being disposed at different distances from the first radiation source.

12. The stand as claimed in claim 9, wherein the radiation detector, which is arranged on the holding apparatus, is operable to be pivoted out of the radiation area of the first radiation source.

13. The stand as claimed in claim 12, wherein the radiation detector is operable to be moved outside the radiation area of the first radiation source to a parked position, which is offset in the opposite direction to the first radiation direction with respect to the examination position.

14. The stand as claimed in claim 13, wherein the radiation detector is operable to be positioned alongside the first radiation source in the parked position, in a lateral direction essentially at right angles to the first radiation direction.

15. A radiation therapy device comprising:
a gantry,
a first radiation source arranged on the gantry, the first radiation source being operable to produce first radiation that can be emitted in a first radiation direction, and
a stand that is arranged on the gantry in order to hold a flat radiation detector, such that the radiation detector is operable to be moved to at least one examination position within a radiation area of the first radiation source, and to a parked position, which is offset in the opposite direction to the first radiation direction with respect to the examination position, outside the radiation area of the first radiation source,
wherein the stand comprises:
a mount,
an intermediate part arranged on the mount, such that the intermediate part is operable to be moved in a lifting direction relative to the mount,
an arm arranged on the intermediate part, such that the arm is operable to pivot relative to the intermediate part about a pivoting axis essentially parallel to the lifting direction, and
a holding apparatus arranged on the arm for holding the radiation detector such that the holding apparatus is operable to be moved in a movement direction essentially at right angles to the first radiation direction relative to the stand.

16. The radiation therapy device as claimed in claim 15, wherein the radiation detector is operable to be moved to different examination positions within the radiation area of the first radiation source, the different examination positions having different distances from the first radiation source.

17. The radiation therapy device as claimed in claim 15, wherein the radiation detector is operable to be positioned essentially alongside the first radiation source in the parked position, in a lateral direction at right angles to the first radiation direction.

18. The radiation therapy device as claimed in claim 15, wherein the stand is arranged on the gantry such that the lifting direction is substantially parallel to the first radiation direction.

19. A radiation therapy device comprising:
a gantry,
a first radiation source disposed on the gantry, the first radiation source being operable to produce first radiation that is emitted in a first radiation direction,
a stand that is disposed on the gantry in order to hold a flat radiation detector, such that the radiation detector can be moved on to at least one examination position within a radiation area of the first radiation source, and to a parked position, which is offset in the opposite direction to the first radiation direction with respect to the examination position, outside the radiation area of the first radiation source,
wherein the stand comprises:
a mount;
an intermediate part arranged on the mount, such that the intermediate part is moved in a lifting direction relative to the mount,
an arm arranged on the intermediate part, such that the arm pivots relative to the intermediate part about a pivoting axis essentially parallel to the lifting direction, and
a holding apparatus for holding the flat radiation detector essentially at right angles to the lifting direction, and
wherein both the first radiation source and the radiation detector are operable to be arranged, in the examination position, on the same side relative to a target volume which can be irradiated with the first radiation.

20. The radiation therapy device as claimed in claim 19, wherein a second radiation source is disposed on the gantry, on a side opposite the radiation detector relative to the target volume.

21. The radiation therapy device as claimed in claim 20, wherein the radiation detector when in its examination position is aligned for detection of second radiation, which is emitted from the second radiation source in the direction of the radiation detector in the examination position.

22. The radiation therapy device as claimed in claim 20, wherein the holding apparatus is operable to be moved in a movement direction essentially at right angles to the first radiation direction relative to the stand.

23. The radiation therapy device as claimed in claim 22, wherein the second radiation source is operable to be pivoted about an axis at right angles to the first radiation direction and at right angles to the movement direction.

24. The radiation therapy device as claimed in claim 20, wherein the second radiation is diagnostic X-ray radiation.

25. The radiation therapy device as claimed in claim 20, comprising: a further radiation detector on the opposite side relative to the radiation detector relative to the target volume for detection of the first radiation.

26. The radiation therapy device as claimed in claim 19, wherein the radiation detector is operable to be moved to different examination positions within the radiation area of the first radiation source, the different examination positions being at different distances from the first radiation source.

27. The radiation therapy device as claimed in claim 19, wherein the radiation detector is operable to be positioned essentially alongside the first radiation source in its parked position, in a lateral direction at right angles to the first radiation direction.

28. The radiation therapy device as claimed in claim 19, wherein the first radiation is therapeutic X-ray radiation.

29. The radiation therapy device as claimed in claim 19, wherein the first radiation passes through the radiation detector.

30. The radiation therapy device as claimed in claim 19, wherein the stand is arranged on the gantry, such that the lifting direction is substantially parallel to the first radiation direction.

* * * * *